United States Patent
Trausch et al.

(10) Patent No.: US 10,945,605 B2
(45) Date of Patent: Mar. 16, 2021

(54) COMBINED RADIOTHERAPY AND MRI APPARATUS

(71) Applicant: ELEKTA LIMITED, Crawley (GB)

(72) Inventors: Gregory Trausch, Billinghurst (GB); Kevin Brown, Horsham (GB); Dan Thompson, East Grinstead (GB)

(73) Assignee: ELEKTA LIMITED, Crawley (GB)

( * ) Notice: Subject to any disclaimer, the term of this patent is extended or adjusted under 35 U.S.C. 154(b) by 367 days.

(21) Appl. No.: 14/887,534

(22) Filed: Oct. 20, 2015

(65) Prior Publication Data

US 2016/0113570 A1    Apr. 28, 2016

(30) Foreign Application Priority Data

Oct. 23, 2014   (GB) ...................................... 1418885

(51) Int. Cl.
*A61B 5/00*   (2006.01)
*A61B 5/055*  (2006.01)
*A61N 5/10*   (2006.01)

(52) U.S. Cl.
CPC .......... *A61B 5/0036* (2018.08); *A61B 5/0555* (2013.01); *A61B 5/4836* (2013.01); *A61N 5/10* (2013.01); *A61N 5/1049* (2013.01); *A61N 2005/1055* (2013.01)

(58) Field of Classification Search
None
See application file for complete search history.

(56) References Cited

U.S. PATENT DOCUMENTS

| | | | |
|---|---|---|---|
| 5,007,425 A | 4/1991 | Vanek et al. | |
| 6,317,619 B1* | 11/2001 | Boernert | G01R 33/341 324/307 |
| 7,230,428 B1 | 6/2007 | Ishii | |
| 7,266,406 B2* | 9/2007 | Kroeckel | G01R 33/34084 324/307 |
| 2008/0064950 A1* | 3/2008 | Ruohonen | A61N 2/006 600/411 |
| 2008/0136412 A1 | 6/2008 | Kato | |
| 2011/0241684 A1* | 10/2011 | Dempsey | A61B 5/055 324/318 |

FOREIGN PATENT DOCUMENTS

| | | |
|---|---|---|
| GB | 2484529 A | 4/2012 |
| WO | WO 90/13045 A1 | 11/1990 |
| WO | WO 2014/044635 A1 | 3/2014 |

OTHER PUBLICATIONS

UK Intellectual Property Office Search Report dated Mar. 26, 2015, 2 pages.

* cited by examiner

*Primary Examiner* — Jonathan Cwern
(74) *Attorney, Agent, or Firm* — Finnegan, Henderson, Farabow, Garrett & Dunner LLP

(57) ABSTRACT

The present invention provides a combined radiotherapy and MRI system in which an imaging coil is mounted on a mechanical arm. The position of the imaging coil is thus known and in embodiments can be controlled to prevent collisions with the patient and unfavourable interactions between the imaging coil and the radiation beam.

15 Claims, 3 Drawing Sheets

COMBINED RADIOTHERAPY AND MRI APPARATUS

CROSS-REFERENCE TO RELATED PATENT APPLICATIONS

This application claims priority from United Kingdom Patent Application No. 1418885.8, filed on Oct. 23, 2014, which is incorporated herein by reference in its entirety.

TECHNICAL FIELD

The present invention relates to a combined radiotherapy and magnetic resonance imaging (MRI) apparatus.

BACKGROUND

Recent developments in the field of radiotherapy have focussed on integrating an imaging system with the therapeutic system. The goal is to provide real-time feedback on the location of an anatomical feature within the patient (e.g. a tumour) such that a therapeutic radiation beam can be more accurately controlled to target that feature.

One suggested approach is to combine a linear accelerator-based therapeutic system with a magnetic resonance imaging (MRI) system within a single apparatus, known as an MRI-Linac. Such apparatus is described in a number of earlier applications by the present Applicant, including U.S. patent application Ser. No. 12/704,944 (publication no 2011/0201918) and PCT publication no 2011/127947. In the systems described in these earlier applications, the patient can be imaged and treated substantially simultaneously while lying in the same position.

One feature of the MRI system is an "imaging coil"—a transmitter/receiver typically comprising a coil and processing electronics—which picks up the low-amplitude electromagnetic signals generated within the patient as part of the MRI process. In a conventional MRI system, the imaging coil is placed directly on the patient so as to maximise the efficiency with which those signals are detected. For example, it is known to manufacture imaging coils using a certain geometry so as to fit closely to certain parts of the human anatomy.

In a combined radiotherapy and MRI system, however, this solution is not possible as the interaction of the radiation beam with the imaging coil generates secondary electrons which would increase the dose in the skin of the patient. An alternative solution is required.

SUMMARY OF INVENTION

According to a first aspect of the present invention, there is provided a system, comprising: a patient support, a radiotherapy device for generating a therapeutic beam of radiation incident upon a treatment volume; and a magnetic resonance imaging (MRI) apparatus for generating imaging data of an imaging volume which encompasses the treatment volume. The MRI apparatus defines a bore in which the patient support can be at least partially positioned, and comprises an imaging coil, fixedly attached to the MRI apparatus by an arm and arranged within the bore, for detecting MRI signals emitted from the imaging volume.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
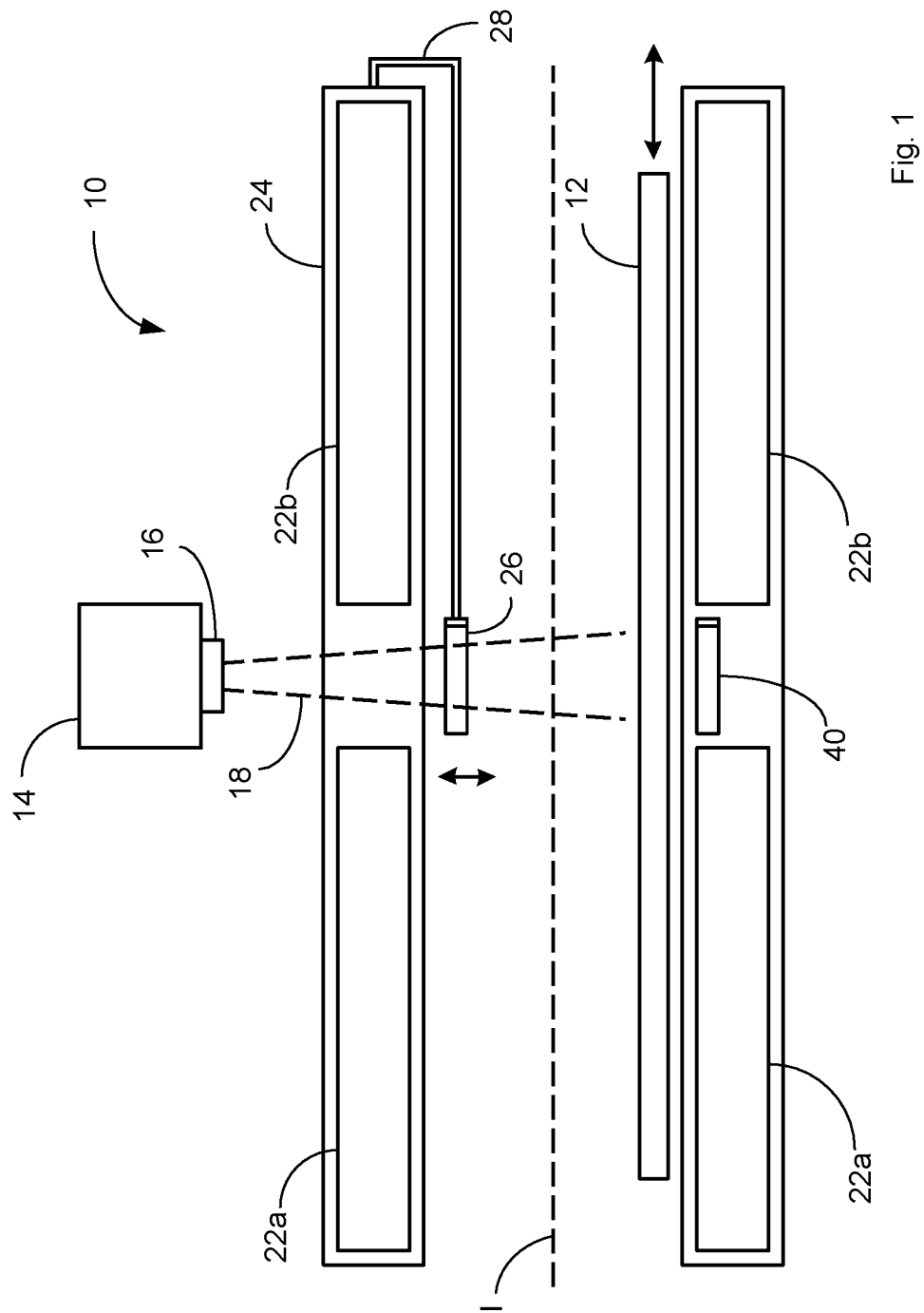
FIG. 1 shows a side view of a combined radiotherapy and MRI system in cross-section according to embodiments of the present invention.
Figure 2:
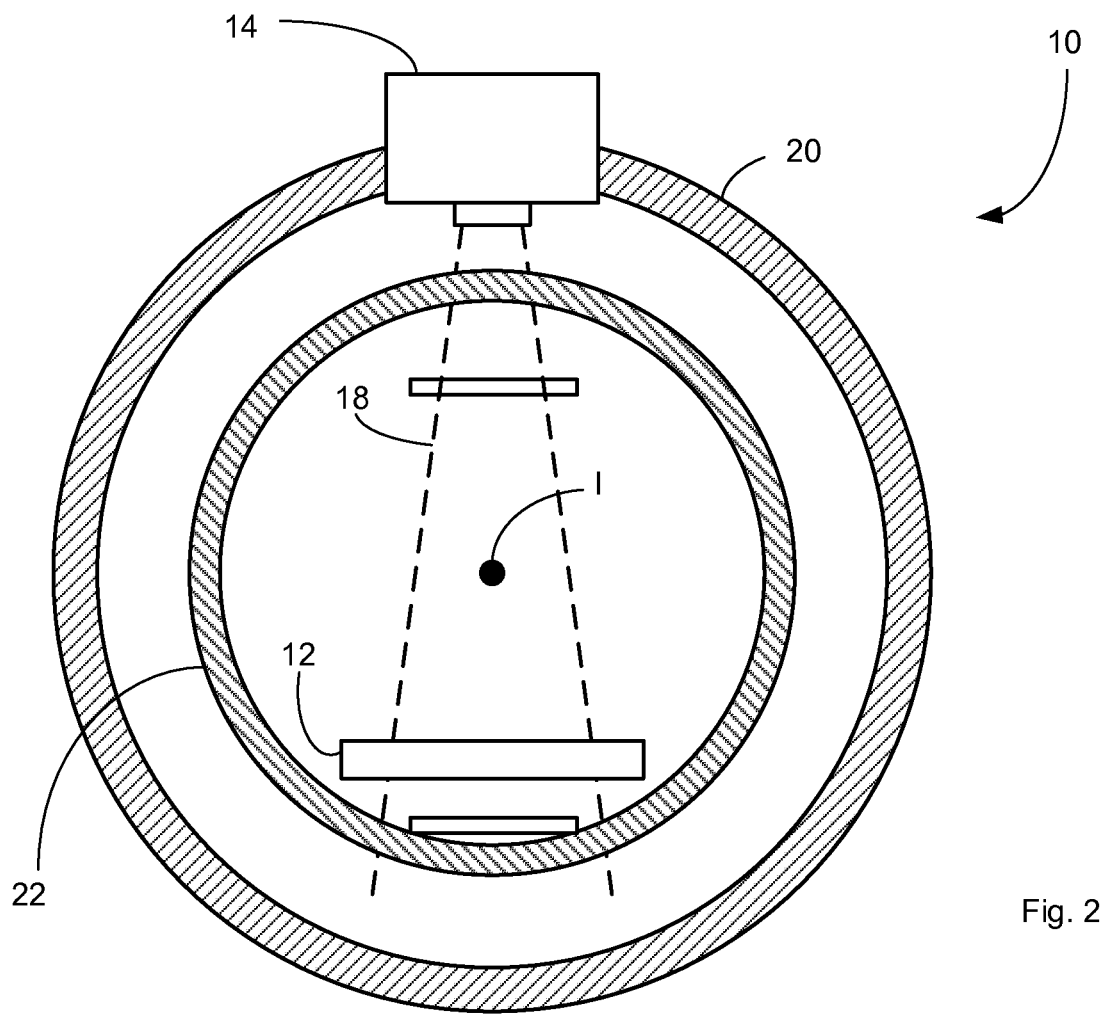
FIG. 2 shows an end view of a combined radiotherapy and MRI system in cross-section according to embodiments of the present invention.

FIGS. 1 and 2 show a combined radiotherapy and MRI system 10 according to embodiments of the present invention. FIG. 1 shows a side view of the system in cross-section, while FIG. 2 shows an end view of the system. Those skilled in the art will appreciate that certain features of the system have been omitted from one or other of the Figures for clarity purposes.

The system comprises a bed 12, for supporting a patient in the apparatus. The bed 12 is movable in a direction parallel to a horizontal axis (labelled "I"), such that a patient resting on the bed can be moved into and out of the apparatus. The bed 12 may form a cantilever section that projects away from a support structure (not illustrated). In one embodiment, the bed 12 is moved along the translation axis relative to the support structure in order to form the cantilever section, i.e. the cantilever section increases in length as the bed is moved and the support structure remains stationary. In other embodiments, the bed 12 may be supported along its length as it moves along the translation axis, such that there is no cantilever section.

The system 10 further comprises a radiotherapy apparatus which delivers doses of radiation to a patient supported by the bed 10. The radiotherapy apparatus comprises a source of radiation 14 and a collimating device 16 (collectively known as a radiation head), which together generate a beam of therapeutic radiation 18. The source of radiation may take any suitable form (e.g. a radioactive source, a linear accelerator, etc), and the beam may be formed using any suitable ionizing radiation, such as x-rays, electrons or protons (for example). The radiation will typically have an energy which is capable of having a therapeutic effect in a patient positioned on the bed 10. For example, a therapeutic x-ray beam may have an energy in excess of 1 MeV.

The collimating device 16 may be any device suitable for collimating the radiation beam to take a desired shape (for example, to conform to the shape of a target within the patient). In one embodiment, the collimating device 16 comprises a multi-leaf collimator, known to those skilled in the art. Such a device comprises one or more banks of elongate leaves (and typically comprises two such banks on opposite sides of the beam), with each leaf being individually moveable into and out of the radiation beam in order to block that part of the beam from reaching the patient. In combination, the leaves collectively act to shape the beam according to a desired cross-section.

The radiation head is mounted on a chassis 20, and configured such that the radiation beam 18 is directed towards and intersects with the axis I. The chassis 20 is continuously rotatable around the axis I, with the point of intersection of the radiation beam with the axis I being known as the "isocentre" of the apparatus. In this way, radiation can be directed towards a patient on the bed 12 from multiple directions, reducing the dose which is delivered to healthy tissue surrounding the target for treatment (e.g. a tumour).

The system 10 further comprises an MRI apparatus, for producing images of a patient positioned on the bed 12. The MRI apparatus includes one or more magnetic coils 22 which act to generate a magnetic field for magnetic resonance imaging. That is, the magnetic field lines generated by operation of the magnetic coil 22 run substantially parallel to the central axis I. The magnetic coils 22 may consist of one or more coils with an axis that runs parallel to, or is coincident with the axis I. The magnetic coils may be split into first and second magnetic coils 22a, 22b, each having a common central axis, but separated by a window which is free of coils. In other embodiments, the magnetic coils 22 may simply be thin enough that they are substantially transparent to radiation of the wavelength generated by the source of radiation 14. In yet further embodiments, the magnetic coils 22 may have a varying pitch, such that the pitch is relatively wide where the coils 22 intersect the radiation beam 18, and relatively narrow in one or more regions outside the radiation beam 18. The magnetic coils may comprise one or more coils for generating a primary magnetic field; one or more coils for generating a gradient magnetic field that is superposed on the primary magnetic field and allows spatial encoding of the protons so that their position can be determined from the frequency at which resonance occurs (the Larmor frequency); and/or one or more active shielding coils, which generate a magnetic field outside the apparatus of approximately equal magnitude and opposite polarity to the magnetic field generated by the primary magnetic coil. The more sensitive parts of the system 10, such as the source of radiation 14, may be positioned in this region outside the coils where the magnetic field is cancelled, at least to a first order.

The coils 22 may be arranged within a housing 24, which can additionally contain a system for keeping the coils cool (e.g. a cryogenic system based on liquid helium or similar). The housing may also allow the system 10 to be kept clean, and reduces patient anxiety whilst undergoing treatment. The internal space of the housing (i.e. inside the coils 22) is often referred to as the "bore".

The radiation source 14 is positioned to emit radiation through the window defined by the two coils 22a, 22b. The radiation beam may take any shape, but in embodiments of the invention can be a fan beam, arranged with the fan's narrow dimension parallel to the axis I. A fan-shaped beam may provide substantial radiation to the patient through the narrow window, meaning that the coils 22a, 22b can be placed closer together than with conventional integrated radiotherapy/imaging systems. This allows the coils 22a, 22b to generate a more homogenous gradient field than would otherwise be the case, increasing the quality of the images obtained by the MRI apparatus.

In use, the MRI system can provide real-time imaging of a patient undergoing therapy, allowing accurate targeting of the treatment volume by the radiation beam 18 (for example through altered collimation by the collimating device 16), or automated shutdown if the patient moves significantly.

One component of the MRI system which has not been discussed above is the RF system. This transmits radio signals towards the patient, and detects the absorption at those frequencies so that the presence and location of protons in the patient can be determined. The RF system may include a single coil that both transmits the radio signals and receives the reflected signals, dedicated transmitting and receiving coils, or multi-element phased array coils, for example. As described above, it is important that the imaging coil be arranged as close to the patient as possible, so as to detect the low-amplitude signals which are emitted by the protons within the patient.

According to embodiments of the invention, the system 10 comprises an imaging coil 26 which is fixedly attached to the MRI apparatus by an arm 28.

Figure 3:
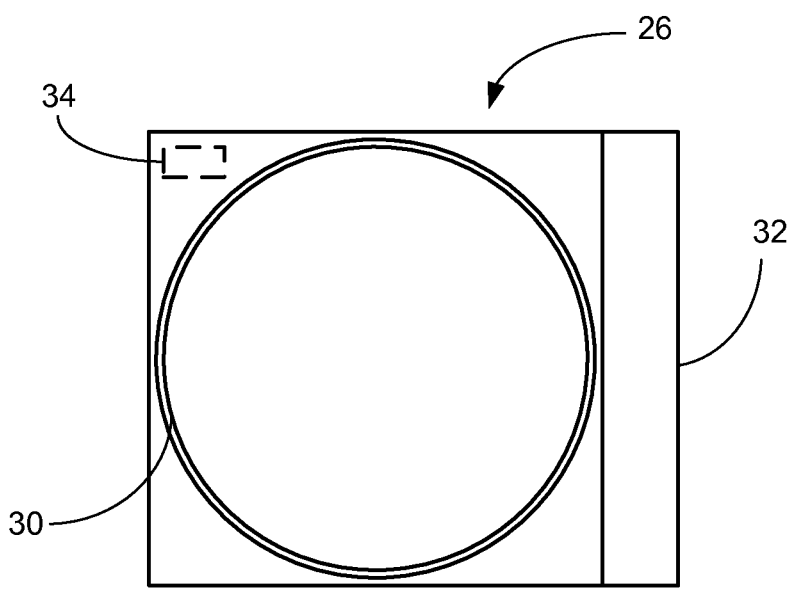
FIG. 3 shows an imaging coil according to embodiments of the present invention.

FIG. 3 shows a plan view of the imaging coil 26. The imaging coil 26 comprises one or more electromagnetic coils 30 and electronic circuitry 32 coupled to the electromagnetic coils, arranged to process the signals received by the electromagnetic coils 30 and/or process signals for transmission by the electromagnetic coils 30. The circuitry 32 therefore comprises a Tx chain and/or an Rx chain comprising one or more amplifiers, and processing circuitry.

As shown in FIG. 3, the circuitry 32 is arranged to one side of the imaging coil 26, with the majority of the planar view taken up by the coil 30. In particular, according to embodiments of the invention, electronic circuitry is not included within the coil 30, above the coil, or below the coil. Instead, the circuitry 32 is placed to the side of the coil 30, and arranged around one or more sides of the imaging coil 26.

The arm 28 is fixedly attached at its near end to the housing 24, or to the frame of the system 10 itself (not illustrated). This fixation point may be at one end of the housing 24, as in the illustrated embodiment, or within the bore itself. At its far end, the arm 28 is coupled to the imaging coil 26. The arm may comprise one or more joints, articulations and/or extending/contracting parts (such as pneumatic pistons, for example), which allow the imaging coil 26 to be moved within and around the bore of the system 10. In addition to manipulating the position of the imaging coil 26, the arm 28 may comprise a mechanism for altering the orientation of the imaging coil 26. The imaging coil 26 can thus be positioned and/or oriented within the bore with a high degree of positional accuracy. In some embodiments, the imaging coil 26 may be attached to the MRI apparatus by more than one arm.

Figure 4:
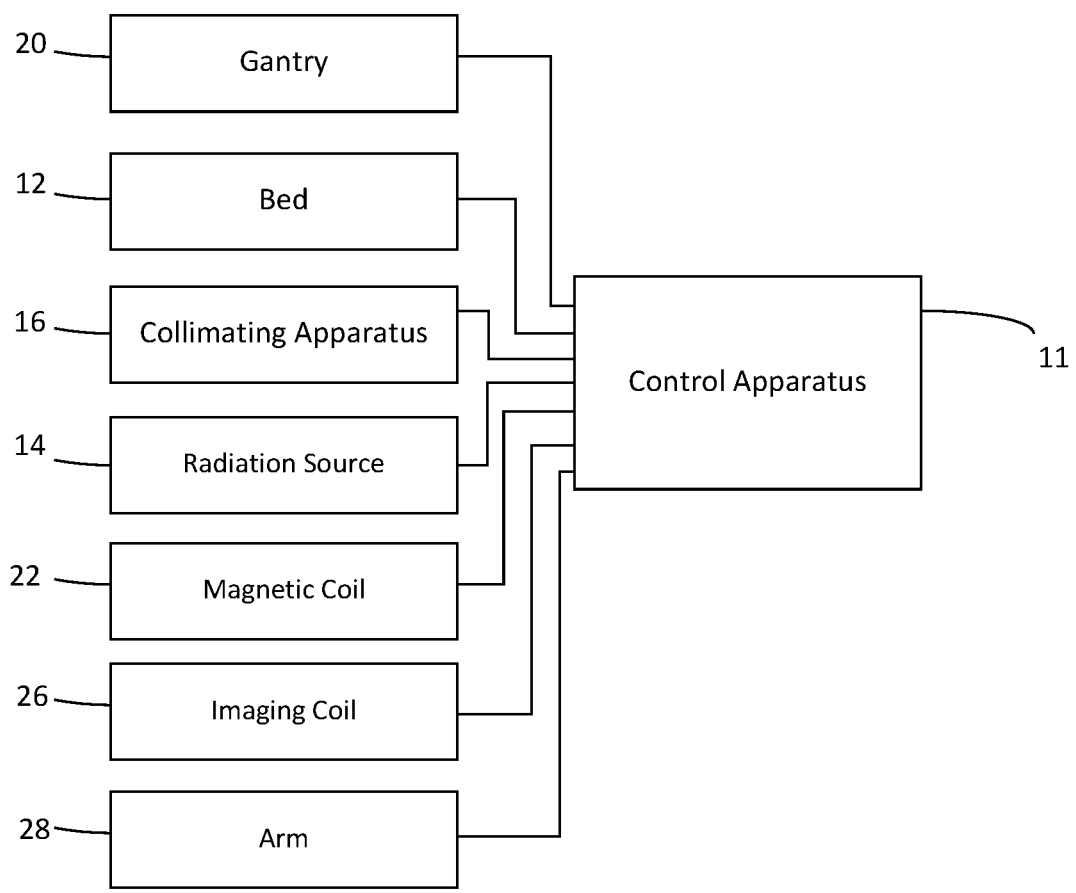
FIG. 4 shows a schematic functional structure for a control apparatus according to embodiments of the present invention.

The system 10 further comprises a control apparatus 11, which is coupled to the various components of the system 10 and controls their operation. The control apparatus will typically comprise a suitably programmed computer, but may also comprise dedicated electronic circuits. As shown in FIG. 4, the control apparatus 11 may also control the MRI parts of the system so as to provide imaging information of the treatment volume of the patient. For example, the control apparatus 11 may control the magnetic coil 22 to generate a magnetic field of a certain strength, and a certain gradient; the control apparatus 11 may control the imaging coil 26 to generate RF signals; and the control apparatus 11 may control the arm 28 to position and/or orient the imaging coil 26 in a certain way. The control apparatus 11 may control the radiotherapy parts of the system according to a predetermined treatment plan and/or in dependence on the imaging data generated by the MRI apparatus. For example, the control apparatus 11 may control the radiation source 14 to generate radiation with a controlled energy, and at a controlled time; the control apparatus 11 may control the collimating apparatus 16 to apply a given collimation to the radiation; the control apparatus 11 may control the gantry 20 to rotate to a certain angle, or to rotate a certain angular distance at a certain rate. The control apparatus 11 may further control the bed 12, so as to position the patient appropriately within the bore.

As discussed above, and as shown in FIGS. 1 and 2, higher imaging quality is achieved when the imaging coil 26 is placed as close to the patient and the source of electromagnetic signals as possible. As the intention of the combined MRI and radiotherapy system is to provide imaging of the volume undergoing treatment, this entails placing the imaging coil 26 close to or in the path of the radiation beam 18. The interaction of the imaging coil with the radiation beam has potential problems, however. For example, secondary electrons generated by interactions between the ionizing radiation and the imaging coil may increase skin dose to the patient if the imaging coil is placed too close to or in contact with the patient. Further, the radiation beam 18 can damage the electronic circuitry 32 which processes the signals received by and transmitted by the coil 30.

According to embodiments of the invention, therefore, the system 10 may be controlled within a set of constraints which serve to reduce or minimize the risks associated with these interactions.

For example, in one embodiment, the arm 28 may be controlled so as to position the imaging coil 26 as close to the patient as possible, but without touching the patient's skin. The imaging coil 26 may be positioned at least a predetermined minimum distance away from the patient, e.g. 5 mm, 10 mm, or 20 mm, to ensure that the patient does not come into contact with the imaging coil by making an expected movement.

In order to achieve this, the imaging coil can be provided with a detection system 34 (shown in FIG. 3), which allows the position of the imaging coil 26 to be determined relative to a patient on the bed 12. The detection system 34 may comprise one or more MRI-imageable markers, such that the MRI system can directly image the detection system and thus determine the position of the imaging coil 26 relative to the patient. In addition, or alternatively, the detection system 34 may comprise a proximity sensor arranged to detect nearby objects. In either case, the detection system may provide feedback to the control apparatus 11 such that the arm 28 is controlled to ensure that the patient and the imaging coil 26 do not come into contact with each other, and remain an appropriate distance apart at all times.

Alternatively, the system 10 may comprise one or more cameras (not illustrated) arranged to view the imaging coil 26 and the patient within the bore, and to provide feedback to the control apparatus 11 such that the arm 28 can be controlled to prevent collisions between the patient and the imaging coil 26. In this embodiment, the imaging coil 26 may not require a detection system 34.

In this way, the position of the imaging coil 26 can be controlled to prevent it from coming into contact with a patient undergoing radiotherapy treatment, while ensuring that the coil 26 is nonetheless as close to the patient as possible to pick up the low-amplitude electromagnetic signals emitted as part of the MRI process.

It can be seen in FIG. 1 that the imaging coil 26 is placed within the path of the radiation beam 18. In fact, according to embodiments of the invention only the electromagnetic coil 30 itself may be placed within the path of the beam; the electronic circuitry 32 is outside the path of the beam 18. According to embodiments of the invention, the arm 28 may be constrained, or the control apparatus 11 may be constrained, such that the electronic circuitry 32 may never enter the path of the beam 18. For example, the arm 28 may be unable to move the imaging coil in a direction along the axis I, and may be constrained to move the imaging coil 26 only vertically (i.e. directly towards and away from the bed 12). In this way, provided the arm 28 has the correct length in a direction parallel to the axis I, the electronic circuitry 32 will never enter the radiation beam 18.

In other embodiments, the arm 28 may be able to move the imaging coil 26 in a direction parallel to the axis I and/or rotate the imaging coil around the axis I, but can be controlled—based on the knowledge of the radiation beam 18 dimensions and the imaging coil 26 position within the control apparatus 11—such that the electronic circuitry 32 does not enter the beam 18.

In this way, according to embodiments of the invention, the position of the imaging coil 26 is always known precisely, and the system can be controlled to avoid harmful interactions between the radiation beam 18 and the electronic circuitry 32.

It will be appreciated by those skilled in the art that the imaging coil 26 need not be placed within the path of the radiation beam 18. When the gantry is rotated to certain angles, for example, the radiation beam 18 may not pass through the imaging coil at all.

The system 10 may comprise one or more further imaging coils, to enhance further the ability to pick up low-amplitude electromagnetic signals emitted from the patient. For example, a second imaging coil 40 may be provided within the housing 24, beneath the bed 12 and in line with the radiation beam 18 (and thus the treatment volume). The second imaging coil 40 may also comprise an electromagnetic coil and processing circuitry, but in the illustrated embodiment is in a fixed position. The fixed position is such that the electronic circuitry cannot fall within the path of the radiation beam.

Those skilled in the art will appreciate that yet further imaging coils (not illustrated) may be provided on respective arms, in a similar manner to the first imaging coil 26. For example, the further imaging coils may be attached to arms fixed to an opposite end of the housing 24 to the arm 28. In this way, the further imaging coils can be controlled to approach the treatment volume from an opposite direction and so cover a wider area.

The present invention thus provides a combined radiotherapy and MRI system in which an imaging coil is mounted on a mechanical arm. The position of the imaging coil is thus known and in embodiments can be precisely controlled to prevent collisions with the patient and unfavourable interactions between the imaging coil and the radiation beam.

Those skilled in the art will appreciate that various amendments and alterations can be made to the embodiments described above without departing from the scope of the invention as defined in the claims appended hereto.

The invention claimed is:

1. A radiotherapy system, comprising:
a patient support;
a radiotherapy device configured to generate a therapeutic beam of radiation incident upon a treatment volume;
a magnetic resonance imaging (MRI) apparatus configured to generate imaging data of an imaging volume which encompasses the treatment volume, the MRI apparatus defining a bore in which the patient support can be at least partially positioned;
an arm; and
an imaging coil, fixedly attached to the MRI apparatus by the arm and arranged within the bore, wherein:
the imaging coil comprises a conducting coil and electronic circuitry coupled to the conducting coil, such that the electronic circuitry is configured to control the conducting coil and is located along a proximal side of the imaging coil with respect to the arm, and wherein the conducting coil and the electronic circuitry are within the bore;

the arm has a length extending within the bore toward the proximal side of the imaging coil and is configured to move relative to and within the bore, to prevent the electronic circuitry from intersecting the beam within the bore; and the imaging coil is configured to detect MRI signals emitted from the imaging volume within the bore.

2. The system according to claim 1, wherein the arm comprises an arm configured such that the movement of the arm adjusts a position of the imaging coil relative to the patient support.

3. The system according to claim 1, further comprising a control system for controlling the arm so as to vary the position of the imaging coil within the bore.

4. The system according to claim 1, further comprising a detection system configured to detect, in use, the position of the imaging coil relative to a patient on the patient support.

5. The system according to claim 4, wherein the detection system comprises a proximity sensor.

6. The system according to claim 4, wherein the detection system comprises MRI-imagable markers mounted on the imaging coil.

7. The system according to claim 4, wherein the position of the imaging coil within the bore is configured to be varied in dependence on the position of the imaging coil relative to the patient.

8. The system according to claim 1, wherein the arm comprises an arm configured such that the movement of the arm adjusts an orientation of the imaging coil.

9. The system according to claim 1, further comprising a plurality of imaging coils.

10. The system according to claim 9, wherein at least one of the imaging coils is fixedly positioned beneath the patient support.

11. The system according to claim 9, further comprising a plurality of arms associated with the imaging coils, wherein at least one of the imaging coils is fixedly attached to the MRI apparatus by an associated one of the arms and is arranged within the bore.

12. The system according to claim 1, wherein the patient support comprises a patient support translatable along a longitudinal axis relative to the bore.

13. A radiotherapy system, comprising:
a radiotherapy device configured to generate a therapeutic beam of radiation incident upon a treatment volume of a patient;
a magnetic resonance imaging (MRI) apparatus having a bore positioned about the treatment volume; and
an imaging coil positioned within the bore and attached to the MRI apparatus by an arm, wherein:
the imaging coil comprises a conducting coil and electronic circuitry coupled to the conducting coil, such that the electronic circuitry is configured to control the conducting coil and is located along a proximal side of the imaging coil with respect to the arm, and wherein the conducting coil and the electronic circuitry are within the bore;
the arm has a length extending within the bore toward the proximal side of the imaging coil and is configured to move relative to and within the bore to adjust the position of the imaging coil to prevent the electronic circuitry from intersecting the beam within the bore; and
the imaging coil is configured to detect MRI signals emitted from an imaging volume within the bore.

14. The system according to claim 13, wherein the electronic circuitry is configured to process at least one of signals received by the conducting coil or signals for transmission by the conducting coil.

15. A radiotherapy system for treating a patient, the system comprising:
a radiotherapy device configured to generate a therapeutic beam of radiation incident upon a treatment volume of the patient;
a magnetic resonance imaging (MRI) apparatus comprising a bore and configured to generate imaging data of an imaging volume encompassing the treatment volume; and
a patient support at least partially positioned within the bore;
an imaging coil attached to the MRI apparatus and not placed directly on the patient, wherein:
the imaging coil comprises a conducting coil and electronic circuitry coupled to the conducting coil, such that the electronic circuitry is configured to control the conducting coil and is located along a proximal side of the imaging coil with respect to the arm, and wherein the conducting coil and the electronic circuitry are within the bore;
the arm has a length extending within the bore toward the proximal side of the imaging coil and is configured to move relative to and within the bore to adjust the position of the imaging coil to prevent the electronic circuitry from intersecting the beam within the bore; and
the imaging coil is configured to detect MRI signals emitted from the imaging volume within the bore.

* * * * *